US00PP33177P2

(12) United States Plant Patent
Olesen et al.

(10) Patent No.: US PP33,177 P2
(45) Date of Patent: Jun. 22, 2021

(54) ***CLEMATIS*PLANT NAMED 'EVIPO098'**

(50) Latin Name: *Clematis viticella*
Varietal Denomination: Evipo098

(71) Applicants: Mogens Nyegaard Olesen, Fredensborg (DK); Raymond J. Evison, Guernsey (GB)

(72) Inventors: Mogens Nyegaard Olesen, Fredensborg (DK); Raymond J. Evison, Guernsey (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,979

(22) Filed: Sep. 3, 2020

(51) Int. Cl.
*A01H 6/72* (2018.01)
*A01H 5/02* (2018.01)

(52) U.S. Cl.
USPC ..... Plt./228

(58) Field of Classification Search
USPC ..... Plt./228
See application file for complete search history.

(56) References Cited

PUBLICATIONS https://www.raymondevisonclematis.com/products/sarah-elizabeth. 2020.*
https://channeleye.media/waitrose-introduces-seven-new-raymond-evison-clematis-varieties/ 2018.*

* cited by examiner

*Primary Examiner* — Annette H Para

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety Denomination: 'Evipo098'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo098' originated as a single seedling from the stated cross.

The new *Clematis* plant may be distinguished from its female seed parent and male pollen parent by the following characteristics. The female seed parent has Red-Purple Group 65B tepals while the new variety has tepals with coloration of Red-Purple Group 62C with intonations of Red-Purple Group 70A. The male seed parent has white tepals while the new variety has red-purple tepals.

The objective of the hybridization of this *Clematis* plant was to create a new and distinct variety for nursery culture with unique qualities such as:

1. Uniform and abundant red-purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo098' was selected by Mogens N. Olesen and Raymond J. Evison in their *Clematis* development program in the Channel Islands, United Kingdom in 2006. Asexual reproduction of 'Evipo098' by means of vegetative cuttings and traditional layering was first performed by Mogens N. Olesen and Raymond J. Evison in the nursery during the summer of 2006. This initial and subsequent asexual propagations have demonstrated that the characteristics of 'Evipo098' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo098'.

Specifically illustrated in FIG. 1 of the drawings is an open flower, tepals detached revealing reproductive flower parts, and a flower bud.

DETAILED DESCRIPTION OF THE VARIETY

Figure 1:
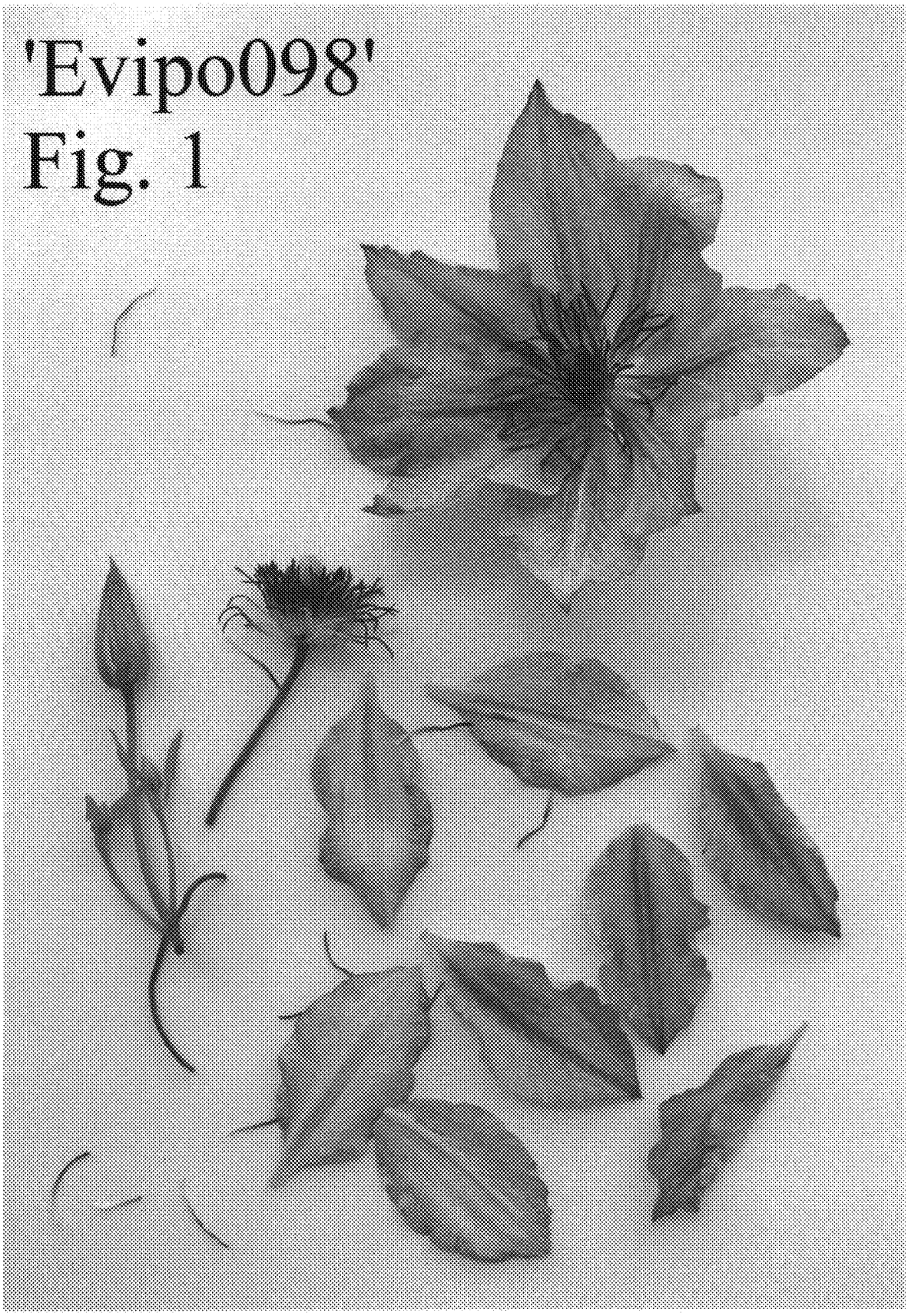
Figure 2:
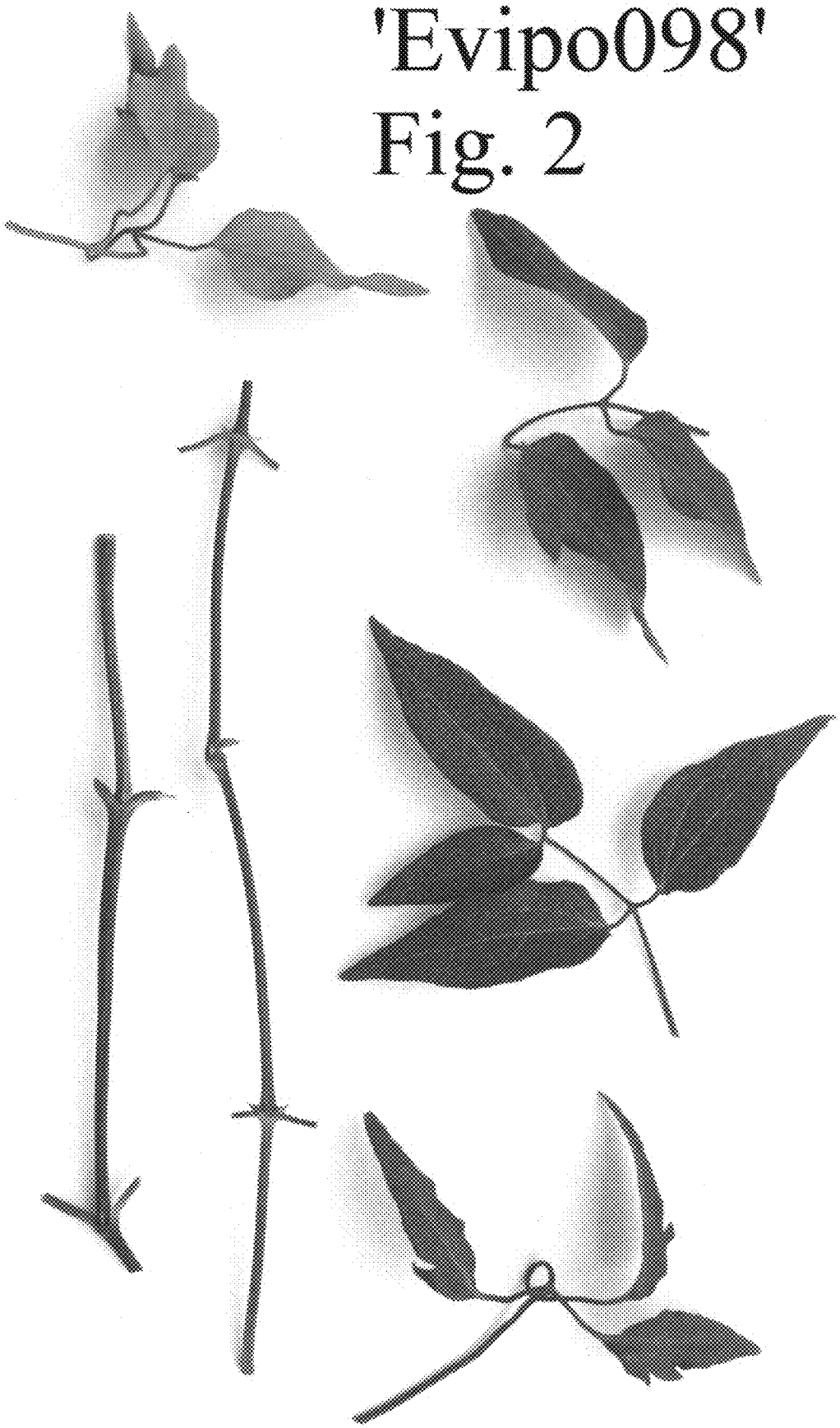
FIG. 2 shows mature and juvenile leaves, and bare stems. Illustrated plants are 2 years of age.

The following is a detailed description of 'Evipo098', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo027' described and illustrated in U.S. Plant Pat. No. 27,281 are compared to 'Evipo098' in Chart 1.

CHART 1

| | 'Evipo098' | 'Evipo027' |
|---|---|---|
| Flower diameter | 135 mm | 145 mm |
| Tepal upper surface after opening | Red-Purple Group 62C with intonations of Red-Purple Group 70A | Red-Purple Group 75A with a central bar Red-Purple Group 77A |
| Tepal count | 8 | 6 to 8 |

Flower and Flower Bud

Blooming habit: Continuous. The natural flowering period is generally from April to September.

Flower bud:
- *Size.*—Normally 37 mm in length. Bud diameter is 11 mm.
- *Bud form.*—Long campanulate, broad based.
- *Bud color.*—Yellow-Green Group 145A.
- *Texture.*—Pubescent.

Pedicel:
- *Surface texture.*—Lightly pubescent.
- *Length.*—On average 60 mm in length with 2 mm diameter.
- *Color.*—Yellow-Green Group 145A.
- *Strength.*—Moderately strong.

Receptacle:
- *Surface texture.*—Lightly pubescent.
- *Shape.*—Broad funnel.
- *Size.*—1 mm (h)×2 mm (w).
- *Color.*—Yellow-Green Group 145A.

Flower arrangement:
- *Location on vine.*—New and old growth.
- *Borne.*—Singly, and in clusters of 3 flowers.

Flower bloom:
- *Size.*—On average, flowers are 135 mm in diameter and 35 mm in depth.
- *Profile.*—Open flowers are flat.
- *Fragrance.*—None.
- *Lasting quality.*—Flowers normally remain up to 14 days on the plant.

Tepals:
- *General tonality.*—Red-Purple Group 65C and Red-Purple Group 70C.
- *Tepal color.*—Upon opening, the upper surface is Red-Purple Group 62C with intonations of Red-Purple Group 70A. The lower surface has a central bar the color of Yellow-Green Group 145D. Adjacent to the central bar Red-Purple Group 69C. At the margin, Red-Purple Group 62C.
- *Quantity.*—Normally 8 tepals.
- *Size.*—70 mm in length by 41 mm wide.
- *Shape.*—Individual tepal shape is elliptic. The tepal apex is Acute. The tepal base is typically acuminate.
- *Apex recurvature.*—None.
- *Tepal cross section.*—Somewhat cupped.
- *Margins.*—Entire. Strong undulations.
- *Persistence.*—Tepals drop off cleanly.

Reproductive organs:
- *Pollen.*—None observed.
- *Anthers.*—Size: 8 mm in length. Color: Greyed-Purple Group N186A. Quantity: On average, 56.
- *Filaments.*—Color: Green-White Group 157A at the base, and Red-Purple Group 71A at the upper portion. Length: 8 mm.
- *Pistils.*—Quantity: On average, 26.
- *Stigmas.*—Superior in location relative to the length of the filaments and the height of the anthers.
- *Styles.*—Color: Yellow-Green Group 145C. Length: 18 mm.

Seed head characteristics: Seed not observed to date.

Plant

Plant form: Climbing.

Plant growth: Moderately vigorous.

Size: Seasons growth attains 80 to 100 cm in height. Average spread is 45 cm.

Stems:
- *Color.*—Juvenile stems are Greyed-Orange Group 177B. Mature stems are Greyed-Orange Group 175A.
- *Internodes.*—On average, 62 to 75 mm between nodes.
- *Length.*—Normally 35 cm from the base of the plant to the flowering portion of the stem.
- *Diameter.*—About 3 mm.
- *Texture.*—Mature stems are ribbed.

Plant foliage:
- *Leaf characteristics.*—Deciduous.
- *Arrangement.*—Ternate.
- *Leaf size.*—Compound leaves are about 115 mm (l)× 120 mm (w). Leaflets are about 55 mm (l)×20 mm (w).
- *Abundance.*—On average leaves per 10 cm of stem.
- *Leaf color.*—Juvenile upper Yellow-Green Group 144A Juvenile lower Yellow-Green Group 144B. Mature upper Yellow-Green Group 146A. Mature lower Yellow-Green Group 147B.
- *Stipules.*—Absent.
- *Petioles.*—Size: Normally 56 mm in length by 1.5 mm diameter. Texture: Smooth. Color: Greyed-Orange Group 171C.
- *Petioloule.*—Size: About 25 mm in length by 1.5 mm diameter. Texture: Smooth. Color: Greyed-Orange Group 171C.
- *Leaflet shape.*—Ovate. The base is rounded, apex acuminate.
- *Margin.*—Entire. Occasionally deep cleft at terminal leaflet.
- *Surface.*—The upper side is smooth, the lower side is smooth.
- *Thickness.*—Moderate.
- *Glossiness.*—Glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo098', substantially as described and illustrated, due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo098'

'Evipo098'